(12) United States Patent
Müller

(10) Patent No.: US 6,537,571 B1
(45) Date of Patent: Mar. 25, 2003

(54) TRANSDERMAL THERAPEUTIC SYSTEM CONTAINING THE ACTIVE SUBSTANCE SCOPOLAMINE BASE

(75) Inventor: Walter Müller, Neuwied (DE)

(73) Assignee: LTS Lohmann Therapie-Systeme AG (DE)

( * ) Notice: Subject to any disclaimer, the term of this patent is extended or adjusted under 35 U.S.C. 154(b) by 0 days.

(21) Appl. No.: 09/485,912
(22) PCT Filed: Aug. 18, 1998
(86) PCT No.: PCT/EP98/05224
§ 371 (c)(1),
(2), (4) Date: Apr. 4, 2000
(87) PCT Pub. No.: WO99/11265
PCT Pub. Date: Mar. 11, 1999

(30) Foreign Application Priority Data

Sep. 4, 1997 (DE) .................................... 197 38 643

(51) Int. Cl.[7] ............................................... A61F 13/02
(52) U.S. Cl. ...................... 424/448; 424/449; 424/443
(58) Field of Search .................... 424/448, 449, 424/443

(56) References Cited

U.S. PATENT DOCUMENTS

| 3,797,494 A | | 3/1974 | Zaffaroni .................... 128/268 |
| 3,903,880 A | * | 9/1975 | Higuchi et al. ............ 128/130 |
| 4,573,996 A | | 3/1986 | Kwiatek et al. |
| 4,655,767 A | * | 4/1987 | Woodard et al. |
| 4,832,953 A | | 5/1989 | Campbell et al. ........... 424/448 |
| RE35,474 E | | 3/1997 | Woodard et al. |
| 5,656,286 A | * | 8/1997 | Miranda et al. ............ 424/448 |
| 5,714,162 A | * | 2/1998 | Muller ....................... 424/448 |

FOREIGN PATENT DOCUMENTS

| DE | 44 38 989 A | 3/1974 |
| DE | 39 08 431 A1 | 9/1990 |
| EP | 0 180 377 A | 5/1986 |
| EP | 0 671 176 A | 9/1995 |
| WO | WO 97 20550 A | 12/1997 |

* cited by examiner

Primary Examiner—Thurman K. Page
Assistant Examiner—Isis Ghali
(74) Attorney, Agent, or Firm—D. Peter Hochberg; Katherine R. Vieyra; Sean Mellino

(57) ABSTRACT

A transdermal therapeutic system containing the active substance scopolamine base and comprising a flexible, active substance-impermeable backing layer, an active substance-containing reservoir layer, a control membrane, a pressure-sensitive adhesive layer for attaching the system onto the skin, as well as a protective film or sheet which is likewise active substance-impermeable and is to be removed prior to application, is characterized in that the reservoir layer as well as the pressure-sensitive adhesive layer are made up of a self-adhesive amino-resistant silicone polymer as base polymer, the control membrane is made up of an ethylene-vinyl acetate copolymer, and that part of the scopolamine base is present, at least in the reservoir layer, in crystalline form.

11 Claims, 1 Drawing Sheet

TRANSDERMAL THERAPEUTIC SYSTEM CONTAINING THE ACTIVE SUBSTANCE SCOPOLAMINE BASE The invention relates to a transdermal therapeutic system containing the active substance scopolamine base and comprising a flexible, active substance-impermeable backing layer, an active substance-containing reservoir layer, a control membrane, a pressure-sensitive adhesive layer for attaching the system onto the skin, as well as a protective film or sheet which is likewise active substance-impermeable and is to be removed prior to application.

Scopolamine is a known substance which is suitable for transdermal application with systemic action, with the aid of a patch. Scopolamine is a so-called antiemetic which is preferably used to avoid nausea and vomitting as, for example, arising from repeated passive changes in balance occurring while travelling.

The therapeutic advantage of transdermal administration consists in that the active substance supply is effected slowly, continuously and in a controlled manner through the transdermal system. Thereby, it is possible to hit the relatively narrow therapeutic window for scopolamine reliably and, on the one hand, to thereby adjust therapeutically effective plasma levels without, on the other hand, having to fear the side effects caused by overdosage, such as, for example, dryness of the mouth, nausea and sensitivity to glare.

U.S. Pat. No. 3,797,494 describes a known transdermal therapeutic system used for administering scopolamine with systemic action. It substantially consists of a backing layer, an active substance reservoir, a microporous membrane, a likewise active substance-containing skin-adhesive layer, and a protective film to be removed prior to use. The reservoir and the skin adhesive layer contain a mixture of polyisobutylenes having various molecular weights and mineral oil. The active substance is dispersed in said mixture as a viscous liquid.

A transdermal system whose active substance-containing components are built up on this basis has, however, considerable disadvantages. Under certain conditions, spontaneous crystallization of the active agent may occur, which has a negative influence on the bioavailability of the active substance in the patch, possibly eliminating it altogether. U.S. Pat. No. 4,832,953 describes in great detail the causes and consequences of such instability. It describes a method making it possible to prevent crystallization by way of subsequent heat treatment of the already packaged patch. The result of this method, however, remains uncertain and uncontrollable. According to the indications given in this document, it is above all scopolamine hydrate which is involved in the unwanted crystallization.

It constitutes a drawback of utmost significance if an active substance contained in a transdermal administration form changes its state of aggregation, under conditions which cannot be defined, at a non-predictable point in time after manufacture, with simultaneous negative influence on bioavailability.

DE-OS 44 38 989 describes a system on the basis of polyacrylate adhesives comprising scopolamine base. In said systems, recrystallization of the active agent is prevented due to the fact that the active substance is present completely dissolved, at a concentration below the saturation limit. The disadvantage here is that the active substance is delivered in vivo with kinetics of the first order and that consequently, in the case of an active substance load of between 1.5 to 2 mg, the permeation rate decreases over the application period of 3 days, and, as a result, is not constant. Only in the case of a higher active substance load would the active substance release be sufficiently constant over the application period, but it still does not take place according to kinetics of zero order. Neither can the problem be solved by the use of membranes as this influences the release rate but not the kind of kinetics.

Figure 1:
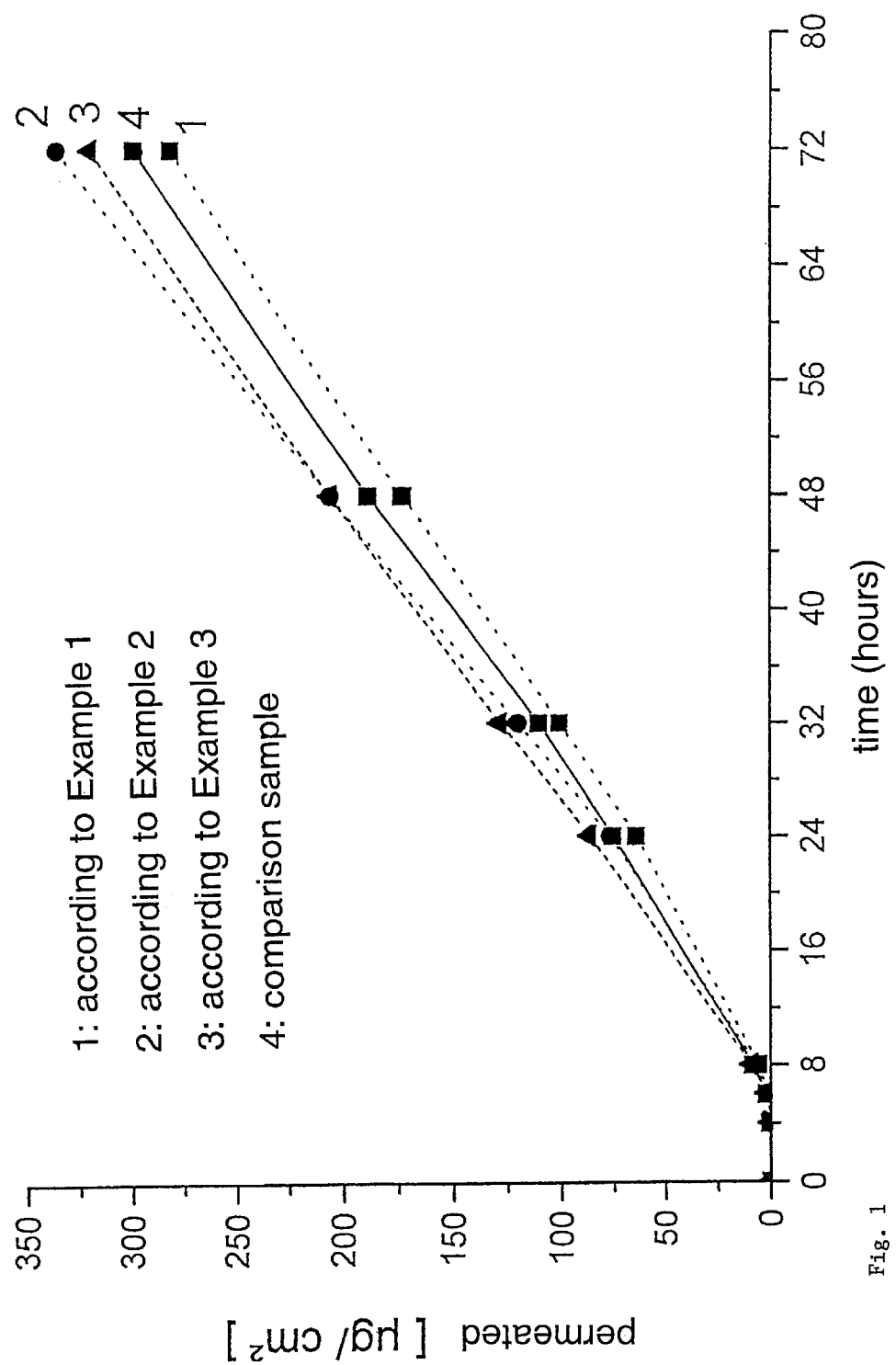
FIG. 1 represents the results of comparative permeation experiments between a commercial comparative sample and three systems according to the invention.

Starting from this state of the art, it is the object of the present invention to provide a transdermal therapeutic system comprising the active substance scopolamine base of the kind mentioned in the introductory portion of claim 1 which avoids the above-mentioned drawbacks of patches according to the prior art and, in particular, a. reliably prevents a recrystallization of the active substance,
b. results in a satisfactory release rate given an active substance load not exceeding 2 mg,
c. after a permeation balance of active substance through the skin has been established, accomplishes a constant release rate over the pre-determined application period and yields constant plasma levels.

Surprisingly, in a transdermal therapeutic system comprising scopolamine base as active substance as mentioned at the beginning of this application, this object is achieved according to the invention in that the reservoir layer as well as the pressure-sensitive adhesive layer are made up of a self-adhesive amino-resistant silicone polymer as base polymer,
the control membrane is made up of an ethylene-vinyl acetate copolymer, and that
part of the scopolamine base is present, at least in the reservoir layer, in crystalline form.

In order to be able to obtain a constant delivery of the active substance over a certain period during which such patches are usually worn of, for example, 3 days, the thermodynamic activity of the active substance in the reservoir must not considerably decrease over the period in which the patch is worn. To achieve this, the concentration of the dissolved portion of scopolamine base contained in the reservoir, respectively in the adhesive layer, must remain constant. This can only be achieved if part of the active substance is initially present in undissolved form and continuously dissolves only during the application period. Surprisingly, it was found that silicone adhesives constitute the optimum base polymer for the above purpose, having a sufficient but not too high solubility for scopolamine base. Aminoresistant silicone adhesives are characterized by their not having any free Si—O—H groups. To obtain said amino-resistant silicones, the Si—O—H groups contained in normal silicone adhesives are converted in a special manufacturing step into Si—O—CH$_3$ groups. Such adhesives are described in EP-A 0 180 377.

Moreover, silicone adhesives are readily soluble in nonpolar solvents, such as, for example, n-heptane, which nonpolar solvents, on the other hand, have an extremely poor solubility for scopolamine base. Consequently, if silicone adhesives are used as base polymer, there is a possibility of incorporating the active substance in a solution of the silicone adhesives, without completely dissolving the active substance. In this case, the temperatures that may be applied during removal of the solvents must be below the melting temperature of scopolamine base, as otherwise the active substance would become dispersed in the adhesive in the form of a subcooled melt. Droplets of the subcooled melt could then recrystallize at an unpredictable time.

However, since the active substance according to the invention is in part present in crystalline form, at least in the reservoir layer, its thermodynamic activity in the polymer remains almost constant once a balance in the active substance release from the reservoir layer into the adhesive layer and in the subsequent dissolution of the crystalline portion has been established. Due to the high diffusion coefficient in the silicone adhesive, the thermodynamic activity in the silicone adhesive is equal to or near the maximum. This means that given a patch size of 2 to 3 cm$^2$, the permeation rate under in vivo conditions would be too high to be able to prevent side effects caused by excessive plasma levels. For this reason it is indispensable to provide a control membrane between reservoir and adhesive layer in order to control the permeation rate. Control membranes on the basis of ethylene vinyl acetate have proved suitable for this purpose. The permeability of these membranes for the active substance can be adjusted in accordance with the thickness and the vinyl acetate content of the membrane. Membranes having a thickness of 30 to 100 $\mu$m and a vinyl acetate content of 4.5 to 19% have proved suitable in the sense of the invention.

It is also of advantage to use substances which increase the rate of permeation through human skin. Such permeation enhancers reduce the barrier effect of the human skin and thereby also the individual impact of the skin on active substance absorption. As a result, permeation enhancers are capable of considerably increasing the control over the active substance absorption through the patch system, thus reducing the variations in permeation rate, which vary from one patient to the other, as well as the fluctuations in the plasma levels resultant therefrom. Fatty acids or fatty alcohols are preferably used. In this context, oleic acid and oleyl alcohol have proved particularly suitable. At the given concentrations, said substances do not cause skin irritations and are compatible with silicone adhesives. An additional advantage of these substances is that they increase the very poor solubility of the scopolamine base in the silicone adhesives.

Other substances, increasing the solubility of the active substance, may also be added to the silicone adhesive, such as polymers, for example. Other additives, such as, for example, silica gels having a high specific surface, may be used in order to improve the physical properties of the adhesive coatings, for example their cohesion.

Examples for the manufacture of a transdermal therapeutic system according to the present invention will be described in the following.

EXAMPLE 1

A Production of the Skin Adhesive Layer 9.5 g scopolamine base are added to 419.3 g of an amino-resistant silicone adhesive having a solids content of 80% (solvent n-heptane) at a mass ratio of ca. 1:44.1 (w/w), and the solution is homogenized by stirring. The solution is coated onto a siliconized polyester film using a doctor knife, and the solvent is removed at 50° C. for 30 min. The coating weight of the dried film is adjusted at 30 g/m$^2$. The dried film is covered with a EVA membrane having a thickness of 50 $\mu$m and a vinyl acetate content of 9%.

B Production of the Reservoir Layer 25.3 g scopolamine base are added to 345.5 g of an amino-resistant silicone adhesive having a solids content of 80% (solvent n-heptane) at a mass ratio of ca. 1:13.66 (w/w), and the solution is homogenized by stirring. The solution is coated onto a siliconized polyester film using a doctor knife and the solvent is removed for 30 minutes at 50° C. The coating weight of the dried film is adjusted at 60 g/m$^2$. The dried film is then covered with a 25 $\mu$m-thik polyester film.

C Production of the Total Laminate

The siliconized polyester film is removed from the reservoir layer manufactured according to B; the reservoir layer is laminated onto the EVA membrane of the skin contact layer manufactured according to A. Patches having a size of 2.5 cm$^2$ are punched out of the total laminate.

EXAMPLE 2

The manufacture is analogous to Example 1; however, 1% (w/w) oleic acid (relative to the solids content) is added to the silicone adhesive solutions.

EXAMPLE 3

The manufacture is analogous to that of Example 1; however, 1% (w/w) oleyl alcohol (relative to the solids content) is added to the silicone adhesive solutions.

The results of comparative permeation experiments between a commercial comparative sample and three systems according to the invention are represented in a diagram according to FIG. 1. Each graph represents a mean value of 3 measurements. The systems were produced according to Examples 1 to 3. For determination of the values so-called Franz' diffusion cells were employed, using human epidermis. The results show that the permeation profiles of the systems according to the invention are almost identical with those of the comparison sample. This proves that the systems according to the invention have the same properties with respect to their permeation rates as the comparison sample, without having the drawbacks with regard to the risk of recrystallization shown by the comparison example.

What is claimed is:

1. A transdermal therapeutic system comprising a flexible, active substance-impermeable backing layer, a reservoir layer containing scopolamine base as a pharmaceutically active substance, a control membrane, a pressure-sensitive adhesive layer for attaching the system onto the skin, and a protective film or sheet which is impermeable to the active substance and which is removed prior to application, wherein said reservoir layer and said pressure sensitive adhesive layer comprise a self-adhesive amino-resistant silicone polymer, said control membrane comprises an ethylene-vinyl acetate copolymer, and part of said scopolamine base is present, at least in the reservoir layer, in crystalline form.

2. The transdermal therapeutic system of claim 1 wherein the control membrane comprises a vinyl acetate content of between 4.5% and 19% and a thickness of between 30 $\mu$m and 100 $\mu$m.

3. The transdermal therapeutic system of claim 1, wherein the reservoir layer has a content of scopolamine base of between 1.0 and 2.5 mg.

4. The transdermal therapeutic system of claim 3 wherein the reservoir layer has a content of scopolamine base of between 1.5 to 2.0 mg.

5. The transdermal therapeutic system of claim 1 wherein the pressure-sensitive adhesive layer has a content of scopolamine base of between 0.2 and 1.0 mg.

6. The transdermal therapeutic system of claim 5 wherein the pressure-sensitive adhesive layer has a content of scopolamine base of between 0.2 to 0.7 mg.

7. The transdermal therapeutic system of claim 1 wherein both the reservoir layer and the pressure-sensitive adhesive layer contain a substance enhancing the permeation rate through human skin.

8. The transdermal therapeutic system of claim 7 wherein the permeation enhancer is a fatty acid or fatty alcohol.

9. The transdermal therapeutic system of claim 8 wherein the permeation enhancer is oleic acid.

10. The transdermal therapeutic system of claim 8 wherein the permeation enhancer is oleyl alcohol.

11. A process for the production of the active substance-containing layer of the transdermal therapeutic system of claim 1 comprising suspending the scopolamine base in a solution of the amino-resistant silicone adhesive; coating the suspension onto a film or sheet; and removing the solvents at temperatures below the melting temperature of the scopolamine base so that the active substance layer is produced.

* * * * *